United States Patent
Miller et al.

(10) Patent No.: US 8,288,970 B2
(45) Date of Patent: Oct. 16, 2012

(54) ADAPTIVE DRIVE SYSTEM USING CURRENT VALUES FOR A PERSONAL CARE APPLIANCE

(75) Inventors: Kevin A. Miller, Bellevue, WA (US);
Ari Lumbantobing, Issaquah, WA (US);
Meindert Lambertus Norg, Canonsburg, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 873 days.

(21) Appl. No.: 12/158,762

(22) PCT Filed: Dec. 14, 2006

(86) PCT No.: PCT/IB2006/054869
§ 371 (c)(1),
(2), (4) Date: Oct. 23, 2008

(87) PCT Pub. No.: WO2007/072365
PCT Pub. Date: Jun. 28, 2007

(65) Prior Publication Data
US 2009/0091275 A1      Apr. 9, 2009

Related U.S. Application Data

(60) Provisional application No. 60/753,093, filed on Dec. 22, 2005.

(51) Int. Cl.
*H02K 33/00* (2006.01)
*H02P 1/00* (2006.01)
*H02P 3/00* (2006.01)

(52) U.S. Cl. .......................... 318/119; 15/22.1

(58) Field of Classification Search .................. 318/119; 15/22.1
See application file for complete search history.

(56) References Cited

U.S. PATENT DOCUMENTS

| 5,613,259 A | * | 3/1997 | Craft et al. | ........... 15/22.1 |
| 5,784,742 A | * | 7/1998 | Giuliani et al. | ........... 15/22.1 |
| 2003/0164658 A1 | | 9/2003 | Saraf | |

FOREIGN PATENT DOCUMENTS

| DE | 10242094 B4 | 4/2004 |
| EP | 0860933 A2 | 8/1998 |
| JP | 2002078368 | 3/2002 |
| JP | 2003210492 A1 | 7/2003 |
| WO | WO04001948 A1 | 12/2003 |

* cited by examiner

*Primary Examiner* — Walter Benson
*Assistant Examiner* — Erick Glass

(57) ABSTRACT

An adaptive system for a personal care appliance, such as a power toothbrush, having a workpiece which is driven through an amplitude of motion by a drive mechanism which includes a stator member includes a circuit (13) for measuring average electrical current through the stator member and stored information (19) in the personal care appliance which relates the average current values through the stator during operation of the device to corresponding amplitude of motion of the workpiece. A processor (17) utilizing a stored program adjusts the operating frequency to produce a stator current value which correlates to the desired amplitude of motion of the workpiece.

34 Claims, 5 Drawing Sheets

ADAPTIVE DRIVE SYSTEM USING CURRENT VALUES FOR A PERSONAL CARE APPLIANCE

This invention relates generally to a system for automatically adjusting the frequency of operation of a personal care appliance to closely match the resonant frequency of the appliance and thereby to produce a desired amplitude of motion of a workpiece portion of the appliance.

It is well known that resonant drive systems, such as those used for driving a workpiece portion of an appliance, for example, a power toothbrush, are highly efficient in producing a reciprocating motion of the workpiece. However, such resonant systems must be driven at or near the frequency of the appliance system in order to operate at the desired high efficiency. This process requires tuning, i.e. matching, the operating frequency of the drive system to the resonant frequency of the appliance.

For appliances which are mass-produced, this frequency matching can be accomplished by either controlling the manufacture of the components of the resonant system to tight standards, so that the actual resonant frequency of the appliance is precisely known, or tuning the operating frequency of the appliance to the actual resonant frequency after manufacture has been completed, or using an adaptive drive system which adjusts the operating frequency depending upon amplitude information provided by a sensing device. All of these approaches, however, generally increase costs, and can produce control issues in production. Accordingly, resonance is typically designed away from in such appliances, resulting in the appliance being easier to manufacture and at a reduced cost.

In those oral care systems which use an adaptive resonant frequency drive, the drive frequency is usually initially set to a known value of resonant frequency for the system, or near that value (within 2-3 Hz), and sensors are then used to adapt the operation of the appliance to actual use conditions. The sensors, however, are usually expensive and difficult to package within a conventional power toothbrush structure.

Accordingly, it is desirable for an oral care appliance, operating at resonance, to have a simple, reliable system for adjusting operating frequency to maintain efficiency of operation, without using sensors or separate mounting equipment.

Accordingly the present invention is a system for adaptive operation of a personal care resonant appliance having a workpiece which is driven through an amplitude of motion by a drive mechanism which includes a stator member, comprising: a circuit within the personal care appliance for measuring average electrical current through the stator member; stored information which relates values of average electrical current through the stator during operation of the device to amplitude of motion of the workpiece, wherein the personal care appliance is characterized by a workpiece amplitude/frequency response curve similar to the stator current/frequency response curve; and a processor operating with a stored program for adjusting the operating frequency of the personal care appliance to produce a current value which correlates with desired amplitude of motion indicating a desired match between the operating frequency and the resonant frequency of the personal care appliance, in accordance with the stored information.

Figure 1:
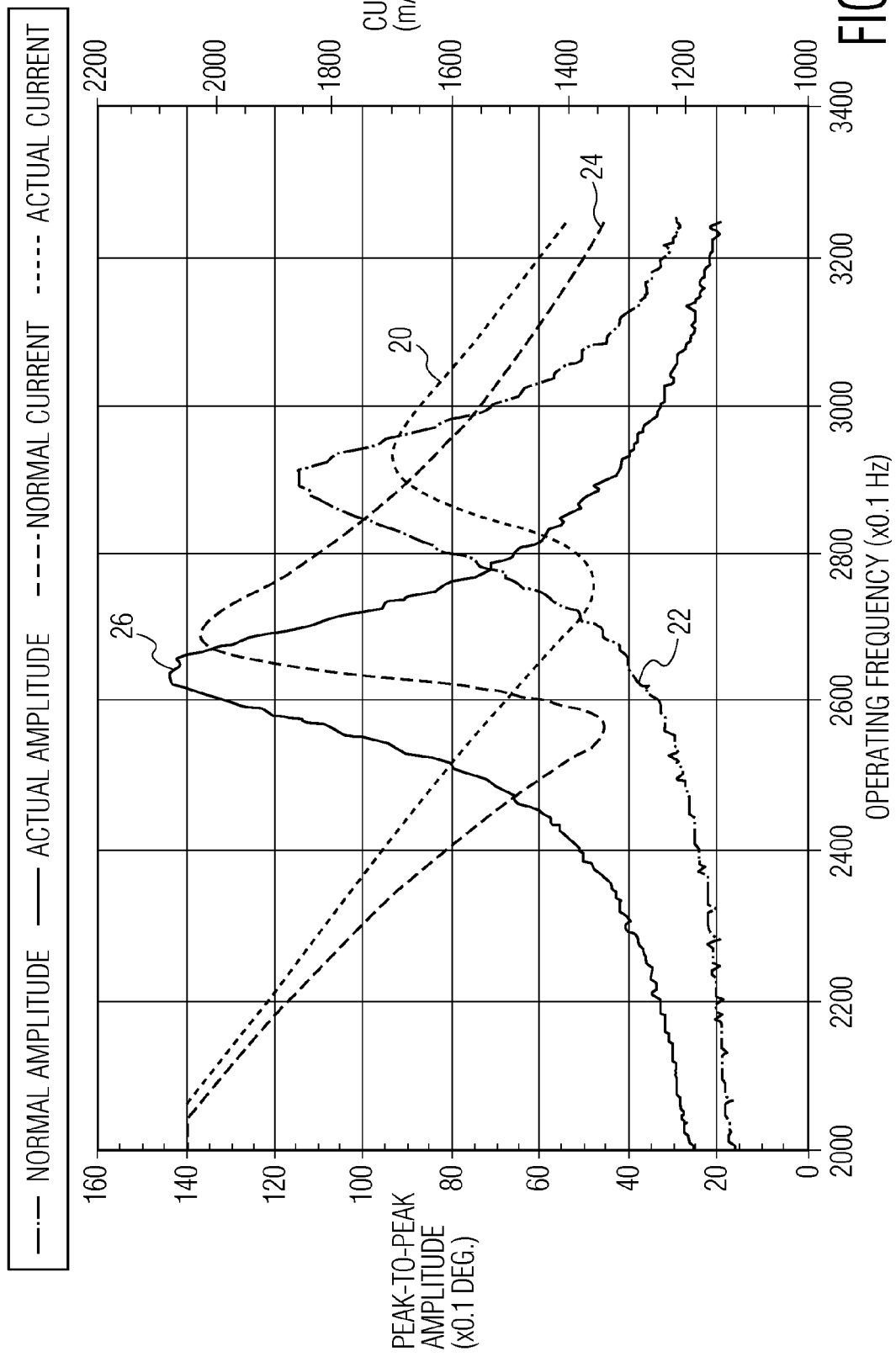
FIG. 1 is a diagram illustrating a factory normalization process between stator current and amplitude values for an actual known appliance and nominal stator current and amplitude values.

For the most efficient operation of a resonant drive system, the operating frequency must be at or near the resonant frequency of the system. It is thus advantageous to tune, i.e. adjust, the operating frequency of the drive system to the resonant frequency of the appliance, both at the time of manufacture of the appliance (at the factory), and during the lifetime of the appliance, in order to both establish and maintain the desired relationship between operating drive frequency and system resonant frequency. However, commonly available methods of tuning such a resonant system are relatively expensive, because they typically require sensors and control circuitry to make the required measurements and adjustments.

An important operating characteristic for appliances, such as power toothbrushes, is the amplitude of movement of the appliance workpiece, e.g. the brushhead for a power toothbrush. A workpiece operating near or at a desired amplitude is important for efficiency purposes as well as for optimum results. Since amplitude near resonance is strongly affected by the relationship between the operating frequency and resonant frequency, a shift between these two frequencies will affect amplitude. The relationship between the two frequencies should be maintained in order to maintain the desired amplitude. However, as discussed above, measurement of workpiece amplitude typically requires expensive equipment and is almost impossible to accomplish during the lifetime of an appliance when it is in the hands of a user.

In the present invention, average current through a stator portion of a stator driven resonant frequency system is used to tune the operation of the appliance. It has been found in some appliances, including power toothbrushes, that the frequency of the peak of the average stator current/frequency response curve is similar to the frequency of the peak of the amplitude/frequency response curve, with a small difference in frequency between them, e.g. 2 Hz, although this difference can be somewhat greater or less. In addition, near resonance, for example, a range of 20 Hz down from resonance, the relative shapes of both curves are similar to each other. These similarities allow the two curves to be correlated, with the average stator current curve being an accurate predictor of the amplitude curve in the above-noted region near resonance. The advantage of average stator current over amplitude is that average stator current can be easily and readily measured, by conventional circuitry within the toothbrush itself, both at the factory and during the lifetime of the toothbrush.

Accordingly, measuring the average current through the stator portion of a stator drive system, and then normalizing the current and amplitude curves of a given appliance to nominal values which represent the accumulated values of a large number of such appliances, permits the use of average stator current as the adjustment criteria for operating frequency, instead of the appliance resonant frequency or workpiece amplitude. The operating frequency can be adjusted to produce a known desired current, which correlates to a desired amplitude which in turn produces the most effective results. This adjustment can be accomplished both at the factory and during the life of the appliance when it is in actual use.

In its simplest form, the operating frequency is adjusted to a fixed average stator current value, e.g. 0.8 amps. If the measured average stator current value is above or below 0.8 amps, the microprocessor in the appliance adjusts the operating frequency until the desired value of average stator current is achieved. This will generally maintain the desired amplitude of workpiece motion. This can be done both at the factory and during the lifetime of the product.

The adjustment can also be more sophisticated, using the curves of the actual device and the nominal curves. Factory normalization will occur as a first step. Factory normalization is designed to compensate for the difference in the current/frequency and amplitude/frequency relationships of an actual appliance to those of a "nominal" appliance, which represent average values for a large number of the same appliance. The microprocessor control in the appliance is based on stored nominal values. The normalization process compensates for differences with the values of an actual appliance.

Figure 2:
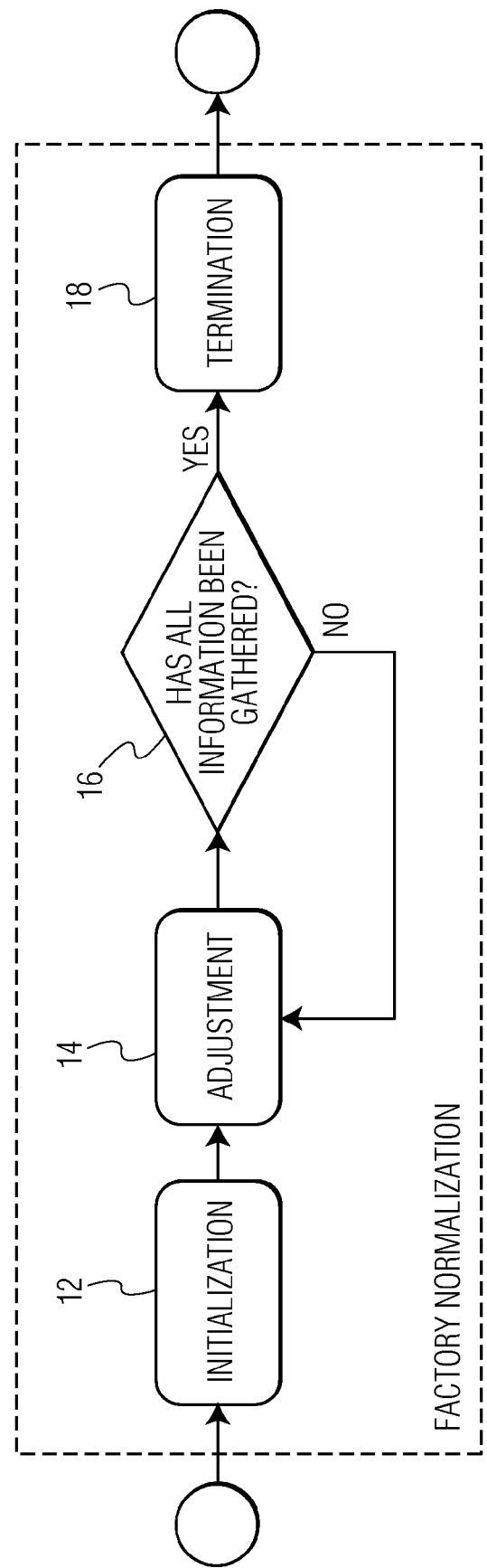
FIG. 2 is a block diagram of the factory normalization process.

FIG. 1 shows an example of current/frequency and amplitude/frequency curves for a particular toothbrush and "nominal" values for such a toothbrush, while FIG. 2 shows the steps in the normalization process. The appliance in the normalization process will learn the relationship between its own current/frequency and amplitude/frequency characteristics relative to the nominal values, which are stored in the appliance.

In FIG. 2, the actual battery voltage V of the appliance under test is obtained, which can be used, if desired, to adjust the normalization constants, as battery voltage will vary somewhat from appliance to appliance. Adjustments are determined for both offset and gain for current and amplitude values. The use of battery voltage-dependent normalization constants allows the adaptive system to work reliably for the user in the later stage of the appliance life, regardless of the condition of the battery. These adjustments due to variation in battery voltage are accomplished in the initialization step 12.

Average stator current and amplitude values of the appliance are then measured for a plurality of frequencies around the typical operating frequency of the appliance, e.g. over a range of approximately 40 Hz. For a power toothbrush, for example, this range could be from 240 to 280 Hz, with a typical value of 262 Hz. A nonlinear regression is then performed in well-known fashion to determine normalization constants for current, amplitude and frequency in order to match the current and amplitude curves of a given appliance to the nominal values. This is shown at step 14. This process continues until all the desired information has been gathered, as indicated at step 16. In some cases, a specific number of measurements are made at different frequencies, without a loop back in the process. This process results in normalization constants of gain and offset for current, amplitude and frequency, in essence relating the current and amplitude curves 20 and 22 of an actual appliance in FIG. 1 to the corresponding nominal values of curves 24 and 26. The normalization constant for frequency values (relating frequency of the actual appliance to nominal frequency) is also determined.

The voltage adjusted normalization constants of gain and offset for both current and amplitude are then stored as well as the normalization constant for frequency, as shown in the termination step 18.

The curves of the actual appliance are now related to the nominal curves and a formula (algorithm) can now be formulated and used which relates the stator current/frequency values to the amplitude/frequency values for a range of operating frequencies, typically 3-7 Hz. This is readily accomplished by one skilled in the art from the curves of FIG. 1.

Then, the average stator current values and the slope of the average stator current/frequency curve at that point can be used to predict the amplitude of the workpiece from the related amplitude/frequency curve. In operation, the processor in the appliance adjusts the operating frequency of the appliance continuously or regularly to provide the most efficient operation for the desired amplitude, e.g. 11°, based on the value of the corresponding average stator current. The appliance is thus operated at peak efficiency, with the operating frequency being adjusted based on average stator current values, i.e. the operating frequency is adjusted toward a value of average stator current that corresponds to the desired amplitude, as determined by the correlation information described above.

Figure 5:
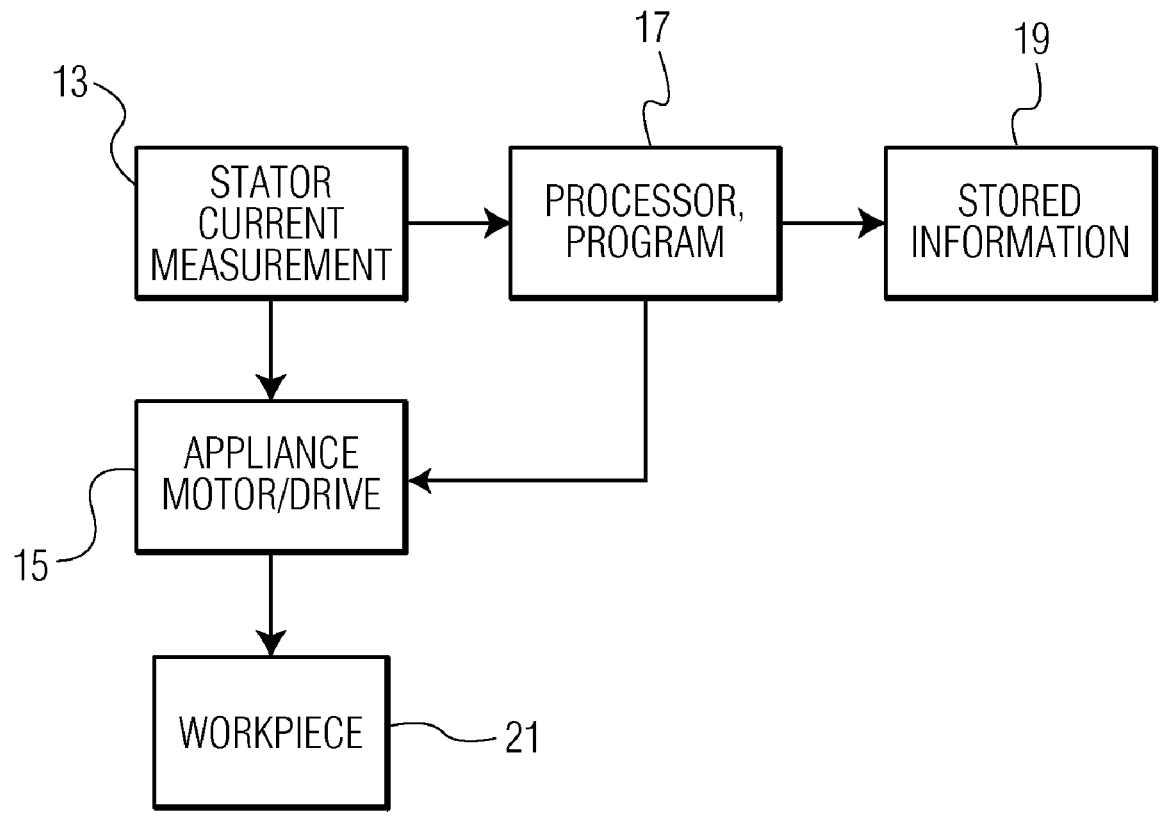
FIG. 5 is a block diagram of the basic system of the present invention within a personal care appliance.

FIG. 5 illustrates the basic system. Average stator current is measured by circuit 13 from the stator 15. Processor 17 processes the average stator current values and adjusts the operating frequency of the motor/drive system for the workpiece 21 accordingly.

The same process of adjusting the operating frequency of the appliance based on average stator current can occur following manufacture, when the device is in actual use, over its lifetime. Stator current is continuously measured and normalized based on the battery voltage present in the appliance at this point; the operating frequency is then adjusted over a small range (approximately 0.5 Hz) in order to produce a desired match between operating frequency and resonant frequency for optimum operating efficiency of the appliance. Making such an adjustment to operating frequency on a regular or continuous basis compensates for changes in the mechanical characteristics of the appliance due to wear or workpiece, e.g. brushhead, replacement.

Figure 4:
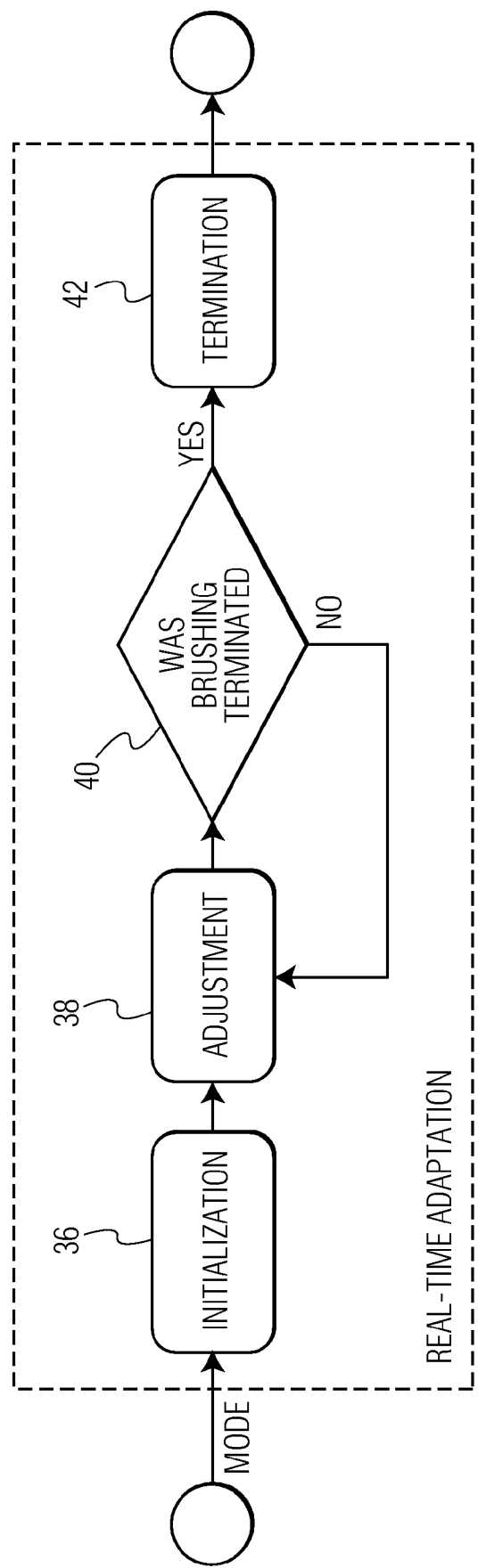
FIG. 4 is a block diagram of the steps in real time adaption of an oral care appliance to load using the present invention.

A block diagram for the life adaption system described above is shown in FIG. 4. During the initialization step 36, the microprocessor in the appliance determines the particular operating mode of the appliance, and adjusts the normalization constants for the appliance based on the battery voltage at that point. The normalized minimum and maximum operating frequencies are then obtained; this establishes a frequency window (difference) of between 3-7 Hz, depending on the appliance. The frequency window may also be different for different operating modes of the appliance. As an example, a power toothbrush may have normal, gentle and massage modes of operation, involving different frequencies and different amplitudes of motion.

The operating frequency will be varied (updated) depending on the specific desired amplitude of motion. As average stator current measurements are made and normalized, if the current is within an acceptable window, then the operating frequency is maintained. If not, the operating frequency is adjusted accordingly for a selected amplitude, as shown at block 38. The adjustment operation is accomplished on a continuous basis until the appliance event, e.g. tooth brushing, is terminated at block 40. The operating frequency information is then added to the stored values in the appliance as the updated operating frequency, for subsequent brushing at block 42.

The above arrangements, using stator current, both relative to a fixed, predetermined stator current value and using related stator current/frequency and amplitude/frequency curves, provides an inexpensive, fast way to accomplish tuning of each appliance during manufacture, at the factory, to the most efficient operating point, and also to provide ongoing adjustment to maintain high efficiency during the life of the appliance. It has also been discovered that the change of average current through the stator during actual operation (loaded) of the device can be used to adjust the operating frequency to maintain maximum desired amplitude under a variety of loads. For instance, in a personal care appliance such as a power toothbrush, the load on the toothbrush during operation may vary typically over a range of 0-250 grams. A constant desired brushhead amplitude, for instance, 11°, although this value can be varied, can be maintained by adjusting the operating frequency depending on the value of average stator current. The adjustment is accomplished in such a manner, as explained below, that a basically flat operating load curve is produced, meaning that the amplitude of motion of the workpiece remains approximately the same over a range of load. Although presently a flat load curve is most desirable, the system and method described herein makes possible custom shape load curves, adapted for specific purposes, or amplitude curves that depend on load.

In one embodiment of load adaption using average stator current as the measured variable, average stator current and the slope of change of the current at two frequencies close together are used to predict amplitude relative to various loads over a selected load range. The stator current and slope at those points on the current/frequency curve are used to vary operating frequency to maintain a constant desired amplitude, i.e. an approximately flat load curve. This information is programmed, i.e. stored, in the appliance. As indicated above, average stator current is measured at two frequencies relatively close together (typically within 0.25-1 Hz), and slope is then calculated for a particular load value. The current and slope values are then used to adjust the operating frequency automatically to maintain the desired amplitude for the immediate load value, by use of the normalized curves and the known relationship between the current/frequency curve and the amplitude/frequency curve discussed above. This is done on a continuous basis, so that as the load changes, the average stator current and slope values will change and the operating frequency will be changed accordingly, to produce the desired amplitude of motion, for instance 11°, as the load changes.

This embodiment, however, has the disadvantage of having to acquire average stator current information over a relatively long, finite period of time to determine an appropriate frequency adjustment for the immediate load, in the face of the need to rapidly adjust the operating frequency in response to the dynamic environment in the mouth where load changes at a very fast pace. In this case, the load curve will not be as flat as desired.

Figure 3:
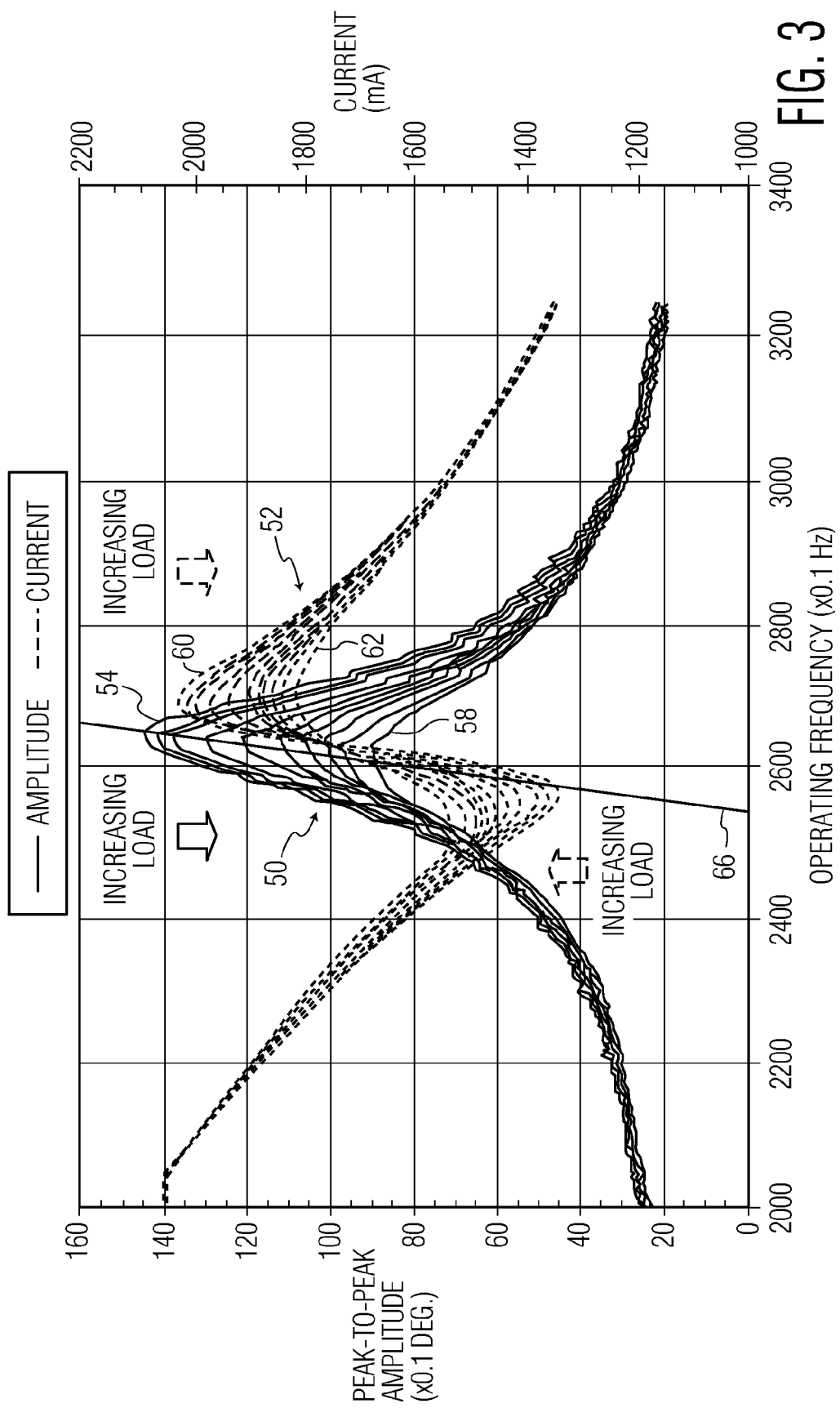
FIG. 3 illustrates the relationship between operating frequency, peak-to-peak amplitude and stator current for a number of different load values on the appliance.

A second embodiment, which does not depend upon determination of current value, slope and follow-on calculations to correlate amplitude, is illustrated in FIG. 3. FIG. 3 is a diagram which includes curves of amplitude versus operating frequency for a plurality of loads (shown as a group at 50), as well as average stator current versus frequency for those same loads (shown as a group at 52). In this particular case, the loads range from 0-250 grams, in increments of 25 grams. In the case of amplitude versus frequency, the unloaded condition is line 54, with the highest excursion, while the line representing the other extreme of a full load of 250 grams is line 56, with the lowest excursion. For average stator current v. frequency values, line 60 has the greatest excursion, in both directions, while line 62, with the least excursion in both directions, represents the current change with frequency for a maximum load of 250 grams. A plurality of load lines between the loaded and unloaded lines (both amplitude and current) are located between the minimum and maximum loads and represent a plurality of different loads.

Straight line 66 in FIG. 3 represents a flat load curve with an amplitude of 11°, while the individual black dots represent the operating frequency to produce an 11° amplitude at the plurality of load values between 0-250 grams in 25 gram increments.

As indicated above, the information in FIG. 3, representing a given toothbrush, is stored in the personal care appliance, e.g. a toothbrush. After the toothbrush is turned on, the normalization constants are first adjusted based on battery voltage, and the stator current is then continuously monitored and normalized in accordance with the normalization constants; as the average stator current changes, it is compared against the stored data of FIG. 3 and the operating frequency 13 adjusted correspondingly to maintain an approximately 11° amplitude of workpiece motion. This can be done very quickly, so that an effective load adaption, i.e. essentially a flat (or custom if desired) load curve, can be produced for a given range of load, even in a very dynamic environment where the load is changing rapidly.

It should be understood that a load range of 0-250 grams and an amplitude of workpiece motion of 11° are examples for a particular appliance, in this case, a power toothbrush. The same principles can be used for other ranges of loads and other amplitudes for other appliances having vibrating workpieces. The system described herein has been found to function well on a center-topped stator with an E-core, as well as an H-bridge driven stator. Other stator-motor configurations can also be used.

The above-described relationship between drive system stator current and workpiece amplitude in a resonant device is thus useful for several functions, including adapting the appliance at the factory to provide most efficient initial operation, adapting the appliance over the lifetime of the appliance, to compensate for on-going wear of the appliance or replacement of the workpiece, and adapting the operation of the appliance as the load changes to provide a constant amplitude over a range of loads on the appliance.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A system for adaptive operation of a personal care resonant appliance having a workpiece which is driven through an amplitude of motion by a motor drive mechanism which includes a stator member, comprising:
   a circuit (13) within the personal care appliance for measuring average electrical current through the stator member (15);
   stored information (10) which relates values of average electrical current through the stator during operation of the device to amplitude of motion of the workpiece, wherein the personal care appliance is characterized by a workpiece amplitude/frequency response curve similar to the stator current/frequency response curve; and
   a processor (17) operating with a stored program for adjusting the operating frequency of the personal care appliance in response to the measured values of stator current to produce an adjusted stator current value which correlates with a desired amplitude of motion indicating a desired match between the operating frequency and the resonant frequency of the personal care appliance, in accordance with the stored information.

2. The system of claim 1, wherein the personal care appliance is a toothbrush.

3. The system of claim 1, wherein the stored information concerning amplitude and current response values is normalized to nominal amplitude and current response values for the personal care appliance.

4. The system of claim 1, wherein said processor operates to control the measuring of electrical current and adjusting the operating frequency of the personal care appliance throughout the life of the personal care appliance, thereby compensating for wear of the appliance and/or replacement of the workpiece.

5. The system of claim 4, wherein the processor operates continuously during the lifetime of the personal care appliance to adjust the operating frequency, when the appliance is in an unloaded condition.

6. The system of claim 2, wherein electrical current values and the slope of the change of current over close values of frequency are measured and then processed to change operating frequency to produce a consistent value of amplitude of workpiece motion over a selected range of loads on the workpiece.

7. The system of claim 6, wherein the range of load is approximately 0-250 grams.

8. The system of claim 7, wherein the range of frequency change relative to load is within the range of 3-7 Hz.

9. The system of claim 2, wherein the stored information includes a plurality of amplitude versus frequency response curves for a selected range of load values, and also a plurality of current/frequency curves for a similar range of load values for the appliance, and further includes information relating the operating frequency correlating a particular load within the range of load to produce a desired amplitude of motion of the workpiece, and wherein the processor operates to change the operating frequency to maintain the desired amplitude of motion as the load changes within the range of load.

10. The system of claim 9, wherein the range of load is approximately 0-250 grams.

11. The system of claim 9, wherein the range of frequency change relative to change of load is between 3 and 7 Hz.

12. A system for initially adapting the operating frequency of a personal care appliance to the resonant frequency of the appliance, the appliance having a workpiece which is driven through an amplitude of motion by a motor drive mechanism which includes a stator member, comprising:
  a circuit (13) for measuring the electrical current through the stator member while the appliance is in an unloaded condition; and
  a system (17, 19) for adjusting the operating frequency of the appliance in response to the measured values of stator current until a stator current value is measured which results in a desired amplitude of motion of the workpiece, as determined by a known relationship between amplitude/frequency and current/frequency curves for the appliance, such that the operating frequency of the appliance can be tuned to a desired relationship relative to the resonant frequency of the appliance, producing the desired amplitude of motion of the workpiece, without measuring the amplitude of motion of the workpiece or the resonant frequency of said appliance.

13. The system of claim 12, wherein the appliance is characterized by a stator current/frequency curve which is offset by a small value of frequency relative to the amplitude/frequency curve.

14. The system of claim 13, wherein the appliance is a power toothbrush.

15. The system of claim 14, wherein the value of frequency is within the range of 3-7 Hz.

16. The system of claim 14, wherein the amplitude/frequency and current/frequency curves are stored within the toothbrush.

17. The system of claim 12, wherein the operating frequency can be adjusted within a range of 0-5 Hz.

18. A system for adaptive operation of a personal care resonant appliance having a workpiece which is driven through an amplitude of motion by a motor drive mechanism which includes a stator member, comprising:
  a circuit (17) within the personal care appliance for measuring average electrical current through the stator member; and
  a processor operating (19) with a stored program in response to the measured values of stator current for adjusting the operating frequency of the personal care appliance to produce a predetermined stator current value which is known to correlate with a desired amplitude of motion indicating a desired match between the operating frequency and the resonant frequency of the personal care appliance.

19. A system of claim 18, wherein the personal care appliance is a power toothbrush.

20. The system of claim 18, wherein said processor operates to control the measuring of stator current and adjust the operating frequency of the personal care appliance throughout the life of the personal care appliance, thereby compensating for wear of the appliance and/or replacement of the workpiece.

21. The system of claim 18, wherein the range of operating frequency change is within the range of 3-7 Hz.

22. A method for adaptive operation of a personal care resonant appliance having a workpiece which is driven through an amplitude of motion by a motor drive mechanism which includes a stator member, comprising the steps of:
  measuring average electrical current through the stator member; and
  processing the measured values of stator current with a stored program and adjusting the operating frequency of the personal care appliance to produce an adjusted stator current value which correlates with a desired amplitude of motion indicating a desired match between the operating frequency and the resonant frequency of the personal care appliance, in accordance with stored information which relates values of average electrical current through the stator during operation of the device to amplitude of motion of the workpiece, wherein the personal care appliance is characterized by a workpiece amplitude/frequency response curve similar to the stator current/frequency response curve.

23. The method of claim 22, wherein the personal care appliance is a toothbrush.

24. The method of claim 22, wherein the stored information concerning amplitude and current response values is normalized to nominal amplitude and current response values for the personal care appliance.

25. The method of claim 22, wherein the step of measuring of electrical current and adjusting the operating frequency of the personal care appliance occurs throughout the life of the personal care appliance, thereby compensating for wear of the appliance and/or replacement of the workpiece.

26. The method of claim 22, wherein the step of processing occurs continuously during the lifetime of the personal care appliance to adjust the operating frequency, when the appliance is in an unloaded condition.

27. The method of claim 23, wherein electrical current values and the slope of the change of current over close values of frequency are measured and then processed to change operating frequency to produce a consistent value of amplitude of workpiece motion over a selected range of loads on the workpiece.

28. The method of claim 27, wherein the range of load is approximately 0-250 grams.

29. The method of claim 28, wherein the range of frequency change relative to load is within the range of 3-7 Hz.

30. The method of claim 23, wherein the stored information includes a plurality of amplitude versus frequency response curves for a selected range of load values, and also a plurality of current/frequency curves for a similar range of load values for the appliance, and further includes information relating the operating frequency correlating a particular load within the range of load to produce a desired amplitude of motion of the workpiece, and wherein the processor operates to change the operating frequency to maintain the desired amplitude of motion as the load changes within the range of load.

31. The method of claim 30, wherein the range of load is approximately 0-250 grams.

32. A method for adaptive operation of a personal care resonant appliance having a workpiece which is driven through an amplitude of motion by a motor drive mechanism which includes a stator member, comprising the steps of:

measuring average electrical current through the stator member; and processing the measured stator current values in accordance with a stored program and adjusting the operating frequency of the personal care appliance to produce a predetermined adjusted stator current value which is known to correlate with a desired amplitude of motion indicating a desired match between the operating frequency and the resonant frequency of the personal care appliance.

33. The method of claim 32, wherein the personal care appliance is a power toothbrush.

34. The method of claim 32, wherein the step of measuring of stator current and adjusting the operating frequency of the personal care appliance occurs throughout the life of the personal care appliance, thereby compensating for wear of the appliance and/or replacement of the workpiece.

* * * * *